United States Patent
Jung et al.

(10) Patent No.: US 12,125,997 B2
(45) Date of Patent: Oct. 22, 2024

(54) SECONDARY BATTERY SYSTEM

(71) Applicant: INCELL CO., LTD., Gwangju (KR)

(72) Inventors: Chang Kwon Jung, Gwangju (KR); Kwon Lee, Gwangju (KR); Choung Yeol Seo, Seoul (KR)

(73) Assignee: INCELL CO., LTD., Gwangju (KR)

( * ) Notice: Subject to any disclaimer, the term of this patent is extended or adjusted under 35 U.S.C. 154(b) by 0 days.

(21) Appl. No.: 18/685,621

(22) PCT Filed: Aug. 16, 2022

(86) PCT No.: PCT/KR2022/012170
§ 371 (c)(1),
(2) Date: Feb. 22, 2024

(87) PCT Pub. No.: WO2023/027404
PCT Pub. Date: Mar. 2, 2023

(65) Prior Publication Data
US 2024/0266629 A1    Aug. 8, 2024

(30) Foreign Application Priority Data

Aug. 23, 2021 (KR) .................. 10-2021-0110836

(51) Int. Cl.
*H01M 10/00* (2006.01)
*A62C 3/16* (2006.01)
(Continued)

(52) U.S. Cl.
CPC .............. *H01M 10/613* (2015.04); *A62C 3/16* (2013.01); *A62C 37/40* (2013.01);
(Continued)

(58) Field of Classification Search
CPC ........... H01M 10/627; H01M 10/6567; H01M 10/655; H01M 10/613; H01M 10/482; H01M 10/4207; Y02E 60/10
See application file for complete search history.

(56) References Cited

U.S. PATENT DOCUMENTS

2020/0373534 A1    11/2020   Simpson et al.

FOREIGN PATENT DOCUMENTS

| CN | 112843543 A | * | 5/2021 | ............... A62C 3/16 |
| JP | 2014090782 A | | 5/2014 | |

(Continued)

OTHER PUBLICATIONS

Wang et al., Temperature Reducing and Fire Extinguishing Device for Battery Pack of Energy Storage Power Station, May 2021, See the Abstract. (Year: 2021).*

*Primary Examiner* — Cynthia H Kelly
*Assistant Examiner* — Monique M Wills
(74) *Attorney, Agent, or Firm* — You & IP, LLC

(57) ABSTRACT

The present invention relates to fire-extinguishing equipment integrated with a secondary battery system for early detection and early extinguishing for reducing the risk of fire spreading inside battery modules, and, more specifically, the present invention comprises: a plurality of battery modules constituting a secondary battery system; module unit fire detection devices mounted inside the modules so as to sense a fire in advance; and integrated fire extinguishing equipment partially coupled to the battery modules so as to directly spray a fire extinguishing agent at the inside of each module, wherein the battery modules include additional members for a cooling effect and the instantaneously supply of a fire-extinguishing agent when a fire is detected.

3 Claims, 14 Drawing Sheets

(51) Int. Cl.
    *A62C 37/40*          (2006.01)
    *H01M 10/613*      (2014.01)
    *H01M 10/643*      (2014.01)
    *H01M 10/6567*    (2014.01)
    *H01M 50/213*     (2021.01)

(52) U.S. Cl.
    CPC ..... *H01M 10/643* (2015.04); *H01M 10/6567* (2015.04); *H01M 50/213* (2021.01); *H01M 2200/10* (2013.01)

(56) References Cited

FOREIGN PATENT DOCUMENTS

| | | |
|---|---|---|
| KR | 10-1312102 B1 | 9/2013 |
| KR | 10-2018-0124439 A | 11/2018 |
| KR | 10-2178601 B1 | 11/2020 |
| KR | 10-2021-0017535 A | 2/2021 |
| KR | 10-2021-0029041 A | 3/2021 |
| KR | 10-2021-0054330 A | 5/2021 |
| KR | 10-2021-0056270 A | 5/2021 |
| KR | 10-2021-0076261 A | 6/2021 |

\* cited by examiner

SECONDARY BATTERY SYSTEM

TECHNICAL FIELD

The present disclosure relates to secondary battery system-integrated fire extinguishing equipment for early sensing and early suppressing for reducing the risk of the diffusion of fire in a battery module. In more detail, the present disclosure includes: a plurality of battery modules constituting a secondary battery system; module unit fire detection devices that sense a rapid increase of temperature in the modules; and integrated fire extinguishing equipment partially coupled to the battery modules and configured to directly spray a fire extinguishing agent into the modules, respectively, in which the battery module includes an additional member for immediate supply of a fire extinguishing agent and a continuous cooling effect when fire is sensed.

BACKGROUND ART

A secondary battery system that is an essential component of energy storage devices that keep electrical energy and uses the electrical energy when needed is in the spotlight as an energy supply and storage source for eco-friendly energy efficiency not only due to the advantage of being able to reduce use of fossil fuel, but also in that byproducts due to use of energy are not produced.

With such potential value and the exponential development of technologies, various types of secondary batteries have been developed, and particularly, an electrochemical lithium-ion battery is the most generally used due to high energy density. According to a secondary battery system using lithium-ion secondary battery cells, it is possible to achieve a battery module by connecting a plurality of lithium-ion battery cells in series/in parallel and achieve a larger capacity by electrically connecting a plurality of battery modules.

In general, a lithium-ion battery cell that is an electrochemical battery type has a low self-discharge rate and a high energy density in comparison to other commercialized types of secondary battery, so the demand for lithium-ion battery cells is exploding. However, inappropriate use, physical abuse, manufacturing defects, etc. of cells induce the electrical and chemical reaction of the electrolyte in a battery up to a dangerous level and increase the pressure in battery cells. Further, electrolyte gas gasified and dissolved through various mechanisms is consequently discharged out of a battery or swelling in which the case of the cells swells is caused due to electrical and chemical actions that are generated inside. Further, thermal runaway in which internal substances dissolved due to accelerated thermal and chemical reactions in cells are discharged in dust and gas types together with high-temperature heat is generated.

When thermal runaway is generated at one battery cell in a battery module, battery cells adjacent to the initially ignited battery cell are thermally damaged due to heat conduction or radiant heat, whereby the adjacent cells ignite by themselves and the thermal runaway starts to spread. Chain ignition of adjacent battery cells causes heat accumulation in a small space and discharge of a large amount of flammable gas, which increases the spread speed and the danger of explosion. As for battery modules composed of cylindrical cells, there is a tendency that the structure supporting a plurality of battery cells melts, whereby a secondary short circuit is generated and the fire in the battery modules rapidly progresses.

In general, a total flooding type of sprinkler system is used as the fire extinguishing equipment of secondary battery systems, and a final spray nozzle is equipped with a heat detector that opens by responding to a specific temperature for a predetermined time to spray a fire extinguishing agent. In this case, the nozzle opens when the scale of a fire reaches a predetermined level, so it may be difficult to suppress a fire at an early stage.

Even though a fire due to thermal runaway is sensed early, it is difficult to make a fire extinguishing agent permeate into a battery module that is dense with a plurality of secondary battery cells, so even though water is supplied in response to early sensing, it is difficult to suppress a fire diffusing in the module and a large amount of fire extinguishing agent is required to suppress a fire spreading out of the module.

Therefore, extinguishing equipment that can sense a fire before fire is diffused by the spread of thermal runaway and can immediately and directly spray a fire extinguishing agent to an ignition point is necessarily required.

RELATED ART DOCUMENTS

Korean Patent Application Publication No. 2021-0017535
Korean Patent Application Publication No. 2021-0029041
Korean Patent Application Publication No. 2021-0054330
Korean Patent Application Publication No. 102178601 호
U.S. Patent Application Publication No. 2020-0373534

DISCLOSURE

Technical Problem

The present disclosure has been made in an effort to solve the problems described above and an objective of the present disclosure is to provide a secondary battery system that reduces the risk of diffusion of fire in a battery module by extinguishing fire by sensing an ignition point in the module at an early stage and directly injecting a fire extinguishing agent to the ignition point.

Another objective of the present disclosure is to provide a secondary battery system that reduces the risk of spread of fire between modules even through fire diffuses in a module.

Technical Solution

In order to achieve the objectives, the present disclosure includes: battery cells; a cell assembly member configuring the battery cells in one unit by connecting the battery cells; a battery module receiving the cell assembly member, and a module unit fire detector disposed in the battery module and sensing a rapid rise of ambient temperature in the module due to gas or flames produced in the module.

The battery module may have a gas discharge port for discharging gas or flames in the module to the outside.

The module unit fire detector may include a gas detector sensing variation of gas concentration due to gas that is discharged from the battery cells.

The battery module may have a fire extinguishing agent spray opening to supply a fire extinguishing agent into the battery module when fire is sensed.

An upper space and a lower space may be formed in the battery module so that a fire extinguishing agent can smoothly move in the module.

The battery module may have up-down through-holes so that a fire extinguishing agent supplied into the module can move down from above.

Further, a water block fence may be provided in the battery module so that a fire extinguishing agent supplied into the module can be kept at a predetermined level.

A spray nozzle inserted in the module through the hole may be disposed in the fire extinguishing agent spray opening.

A distal end portion of the spray nozzle may be connected to a tube having a predetermined length.

A predetermined portion of an open end of the tube may be filled with a heat-sensitive material so that the tube opens when a predetermined temperature is reached.

The battery module may include a plurality of battery modules arranged in a predetermined direction.

Fire extinguishing equipment for supplying a fire extinguishing agent into the battery module includes fire extinguishing equipment composed of a fire extinguishing tank receiving a fire extinguishing agent, a fire extinguishing pump and a fire extinguishing pipeline for moving the fire extinguishing agent into the battery modules from the fire extinguishing tank, a valve opening such that the fire extinguishing agent is supplied to the battery modules through the pipeline, and a control unit receiving a signal from the module unit fire detector and controlling the fire extinguishing pump.

The valve may be an active on/off valve that is normally maintained in a closed state, and is opened (automatically by control of a valve control member) when fire is sensed.

The fire extinguishing control unit may include a valve control member controlling the active on/off valve.

Further, a battery rack includes a metal container for receiving the battery modules.

The pipeline may be composed of a common pipeline extending from the fire extinguishing tank to an upper portion of a battery space receiving the battery rack, a horizontal main pipeline horizontally connected from the upper portion of the battery space, a vertical cross pipeline vertically diverging from the horizontal main pipeline and extending along a side of the battery rack, an branch pipelines diverging from the vertical cross pipeline at heights respectively corresponding to module fire extinguishing agent spray openings, and connected in parallel to the spray nozzles, respectively.

An active on/off valve disposed on any portion of the vertical cross pipeline and opening the vertical cross pipeline so that a fire extinguishing agent is supplied to at least one or more branch pipelines diverging from the vertical cross pipeline may be provided.

In order to achieve the objectives, a secondary battery system according to the present disclosure may include two or more the battery rack.

A signal relay that receives a signal from a fire detector of a module received in the battery rack and transmits the signal to the fire extinguishing control unit may be provided for each of the battery racks.

Advantageous Effects

Since a fire detector is provided in the battery module of the present disclosure having the configuration described above, it is possible to sense thermal runaway, which is generated in the battery module, at an early stage.

That is, in the related art, fire detectors are disposed outside a battery module, that is, at a predetermined position in a space in which a module is received, so the fire detectors can sense fire in the module when the fire spreads at a predetermined level due to the distance from an ignition origin and the detectors in the module. In particular, when a battery module is composed of cylindrical battery cells, the heat energy emitted from one battery cell is low due to thermal runaway in comparison to large-scale battery cells, so it is possible to sense fire only when ignition is serially generated to adjacent battery cells and the scale of the fire reaches a predetermined level. Accordingly, the present disclosure includes a fire detector that senses heat in a battery module, so it is possible to greatly reduce the ratio of failure in sensing of fire before thermal runaway spreads around.

Further, according to a configuration of the present disclosure, since a gas detector is added to a module unit fire detector, it is possible to increase the reliability and accuracy in diagnosis of fire in a module.

Further, in a battery module according to a configuration of the present disclosure, when a fire extinguishing agent that is sprayed into the module contains water, the fire extinguishing agent moves along an upper space in the module and is kept at a predetermined level from the floor of the module for a predetermined time, so a continuous cooling effect is provided for the entire of the inside of the module, whereby it is possible to prevent thermal runaway from spreading to surrounding battery cells.

Further, it is possible to prevent diffusion of fire due to re-ignition after a predetermined time passes due to energy remaining in a damaged battery cell even after the fire is suppressed at an early stage.

Further, according to a configuration of the present disclosure, a nozzle that sprays a fire extinguishing agent into a module is configured in a normal open type. In general, a temperature response unit is disposed at an end of a nozzle and the nozzle is configured to open when it is exposed to a predetermined temperature for a predetermined time. A fire extinguishing nozzle (temperature response-type nozzle) having such a temperature sensing unit is disposed outside a battery module or disposed in an opening at a side of a battery module, and in this case, the temperature response unit is configured to respond to heat that is discharged out of the module, so it may be difficult to immediately open the nozzle. In particular, when cylindrical battery cells are provided, the heat that is emitted by thermal runaway generated at one cell may not be enough to open a temperature response unit unless the temperature response unit is positioned at a short distance, so the timing of early suppression may be missed. However, a normal open-type spray nozzle can immediately spray a fire extinguishing agent into a module without delay when fire is sensed. A normal open-type spray nozzle has a simple structure and is easy to install, so it has also the advantage of being able to reduce the manufacturing and installation costs.

Further, in order to spray a fire extinguishing agent, which is supplied through a spray nozzle, uniformly into a module within a short time, a distal end portion of the spray nozzle may be connected to a first end of an insulating tube having a predetermined length and a second end of the tube may be positioned in the module. In this configuration, a plurality of open holes may be provided in the longitudinal direction of the tube so that a fire extinguishing agent is sprayed through a side of the tube while moving. In this case, the fire extinguishing agent can be uniformly supplied into the module through not only the open hole at the distal end of the tube, but also the open holes on the side of the tube.

Further, according to a configuration of the present disclosure, since an active on/off valve is disposed at a predetermined position of a fire extinguishing pipeline, the pipeline on which the active on/off valve is disposed can be opened when fire is sensed so that a fire extinguishing agent is supplied to branch pipelines diverging from the pipeline. Accordingly, the fire extinguishing agent is put into not only the module at which thermal runaway started, but also modules sharing the pipeline opened by the open active on/off valve, so even though fire spreads between modules due to diffusion of fire in the problematic module, it is possible to limit the number of modules to which fire spreads, whereby there is the advantage of effectively preventing fire from spreading outside a battery rack.

However, in this case, a large amount of fire extinguishing agent may be needed, and when there is no enough space for keeping a large amount of fire extinguishing agent, a distal end portion of an open-type spray nozzle according to another embodiment of the present disclosure may be inserted in a first end of an insulating tube and a second end of the tube through which a fire extinguishing agent is sprayed may be positioned in a module. An end of the tube through which a fire extinguishing agent is finally sprayed may be filled with a heat-sensitive material that melts at a predetermined temperature. Since the heat-sensitive material is disposed at a predetermined position in a module, it is possible to relatively approach close to the potential position of a fire origin in the module, so it is possible to reduce the time that is taken to open the tube through melting of the heat-sensitive material. In this case, it is possible to spray a fire extinguishing agent only to a problematic module, unlike an open-type nozzle, and it takes short time to open a nozzle in comparison to a temperature response-type nozzle disposed outside a module, so early suppression is possible.

MODE FOR INVENTION

Figure 1:
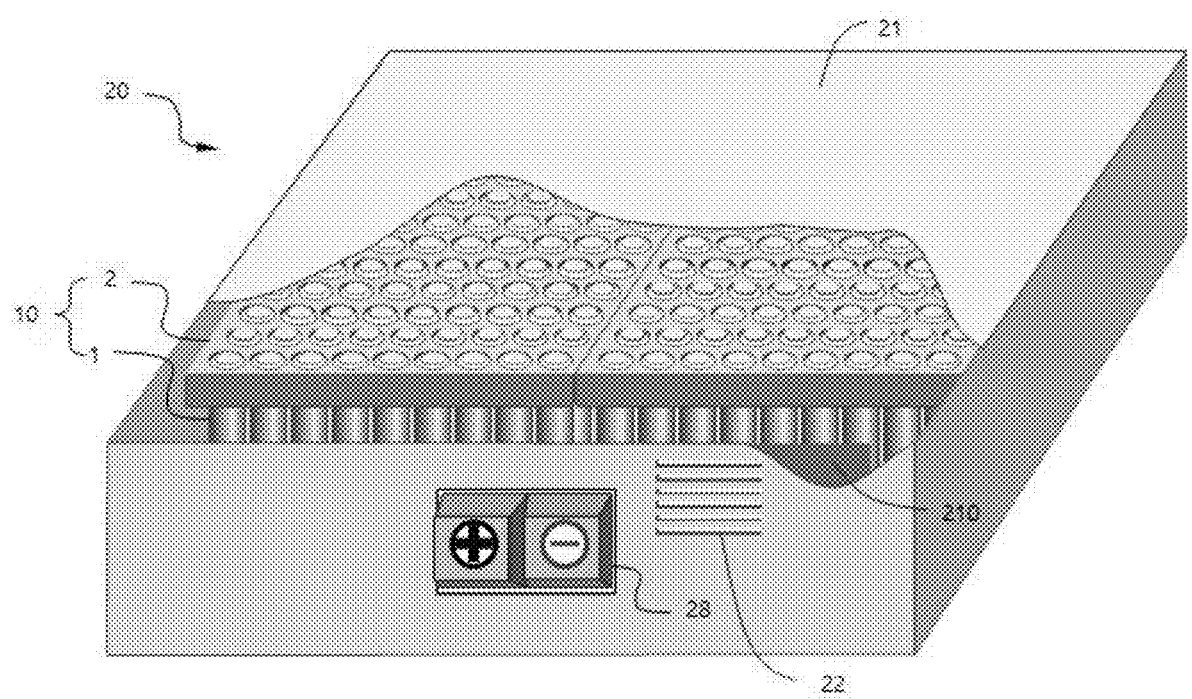
FIG. 1 is a schematic front perspective view of a battery module that shows the inside of a partial cut portion according to an embodiment of the present disclosure.

Exemplary embodiments of the present disclosure will be described with reference to the accompanying drawings to help sufficiently understand the present disclosure. Embodiments of the present disclosure may be modified in various ways and the scope of the present disclosure should not be construed as being limited to the embodiments to be described below. Embodiments are provided to more completely explain the present disclosure to those skilled in the art. Accordingly, the shapes of components may be exaggerated in the drawings to emphasize clearer description. It should be noted that same components may be indicated by same reference numerals in the drawings. Further, when functions and configurations of components well known in the art may make the gist of the present disclosure unclear, a detailed description of the components will be omitted.

Therefore, it should be understood that embodiments described herein and the configurations shown in the drawings are only the most preferable examples of the present disclosure and do not represent the entire of the spirit of the present disclosure.

The present disclosure includes a battery module 20 composed of battery cells 1, a battery rack 30, etc.

In detail, the battery module 20 is composed of a cell assembly member 10 composed of a plurality of battery cells 1 and a module housing receiving at least one or more the cell assemblies. The secondary battery cell 1 may be polyhedral, pouch-shaped, and cylindrical battery cells.

As shown in FIG. 1, when cylindrical battery cells are used, the battery module 20 is configured to receive at least one or more cell assemblies 10. The cell assembly member has cell holders 2 physically fixing the upper portion and the lower portion of a plurality of battery cells 1 and taps (not shown) connecting the cell holders 2 and terminal portions of the battery cells. The cell assemblies in the module are connected through bus bars (not shown), whereby the energy capacity of the module is determined. The module may have a terminal 28, through which electrical energy is finally input/output, on a side of the module.

The battery module includes a module unit fire detector 210 that senses ambient temperature inside the module that is changed by gas or flames produced by thermal runaway in the module, and the module unit fire detector is disposed in the module.

The module unit fire detector 210 is configured as a temperature sensor that senses ambient temperature and can sense generation of fire by determining a thermal runaway event when the instantaneous temperature rise rate of temperature that is sensed by the temperature sensor is larger than an allowable temperature rise rate.

According to small-capacity battery cells such as a cylindrical type, the immanent electrical energy capacity is small in comparison to large-capacity battery cells, so the thermal energy that is emitted by thermal runaway is relatively low. Further, since flames are discharged by a high increased pressure inside the battery cell case, the flames can go out of the module 20 within 1 to 3 seconds. Accordingly, the response time of a sensor that senses temperature is very important to sense instantaneous variation of ambient temperature due to gas or flames that are quickly discharged. That is, when the response time of the sensor is longer than the instantaneous variation of ambient temperature by thermal runaway, sensing the thermal runaway may fail. Accordingly, in order to increase the reliability and accuracy in sensing of fire in the battery module 20, a thermocouple, thermistor, or optical fiber temperature sensor of which the response time is shorter than the time for which flames go out of a module may be used.

Further, the module unit fire detector 210 may include a gas detector that can sense gas that is discharged from the battery cells before generation of runaway. When the gas detector senses a rise of gas concentration and there is a rapid rise of gas concentration, the gas detector determines a gas detection event and determines sensing of fire in the module 20 by combining the gas detection event with a temperature rise event signal of the module unit fire detector 210, thereby being able to increase the reliability of a fire sensing signal.

The battery module may have a gas discharge port 22 having openings on one side or two sides in the front-rear direction of the module to discharge gas or flames to the outside.

Figure 2:
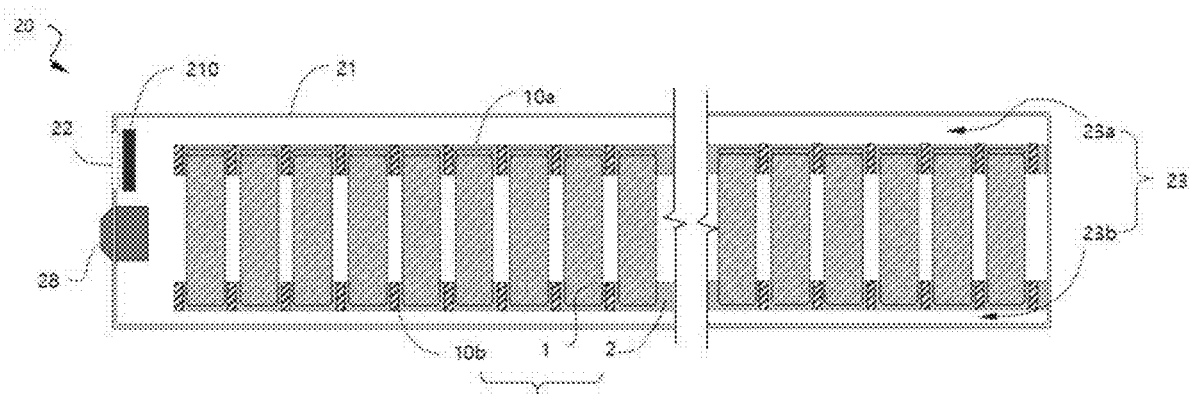
FIG. 2 is a cross-sectional view schematically showing a cross-section of a side of the battery module according to an embodiment of the present disclosure.

In order to smoothly discharge gas or flames produced by thermal runaway, the battery module 20 may have a space 23 between the top 10a or the bottom 10b of the cell assembly member 10 and the module case housing 21. In detail, as shown in FIG. 2, the gap from the module housing case is maintained by a plurality of spacing members (not shown) protruding from the top and the bottom of the cell assembly member, whereby the internal space 23 is formed.

The space 23 (23a, 23b) has the purpose of securing an insulation distance between the cell assembly member 10 and the module case 21 and providing a gas path for discharging gas, which is discharged from the cell assembly member 10, out of the battery module 20. For this reason, the module unit fire detector 210 may be positioned around the gas discharge port 22 positioned at the distal end of the path through which gas or flames are discharged to the outside.

As shown in FIG. 1, a fire extinguishing agent may have difficulty in quickly permeating and moving to an ignition origin due to the battery cells 1 densely disposed in the battery module 20. Accordingly, the space 23 (23a, 23b) shown in FIG. 2 may be used as a path of a fire extinguishing agent that is supplied into the module to suppress fire in the module 20.

As the fire extinguishing agent 200, water, water having a fire extinguishing agent substance added, air foam fire extinguishing agent substance containing foam having high expansivity, or the like may be used.

Figure 3:
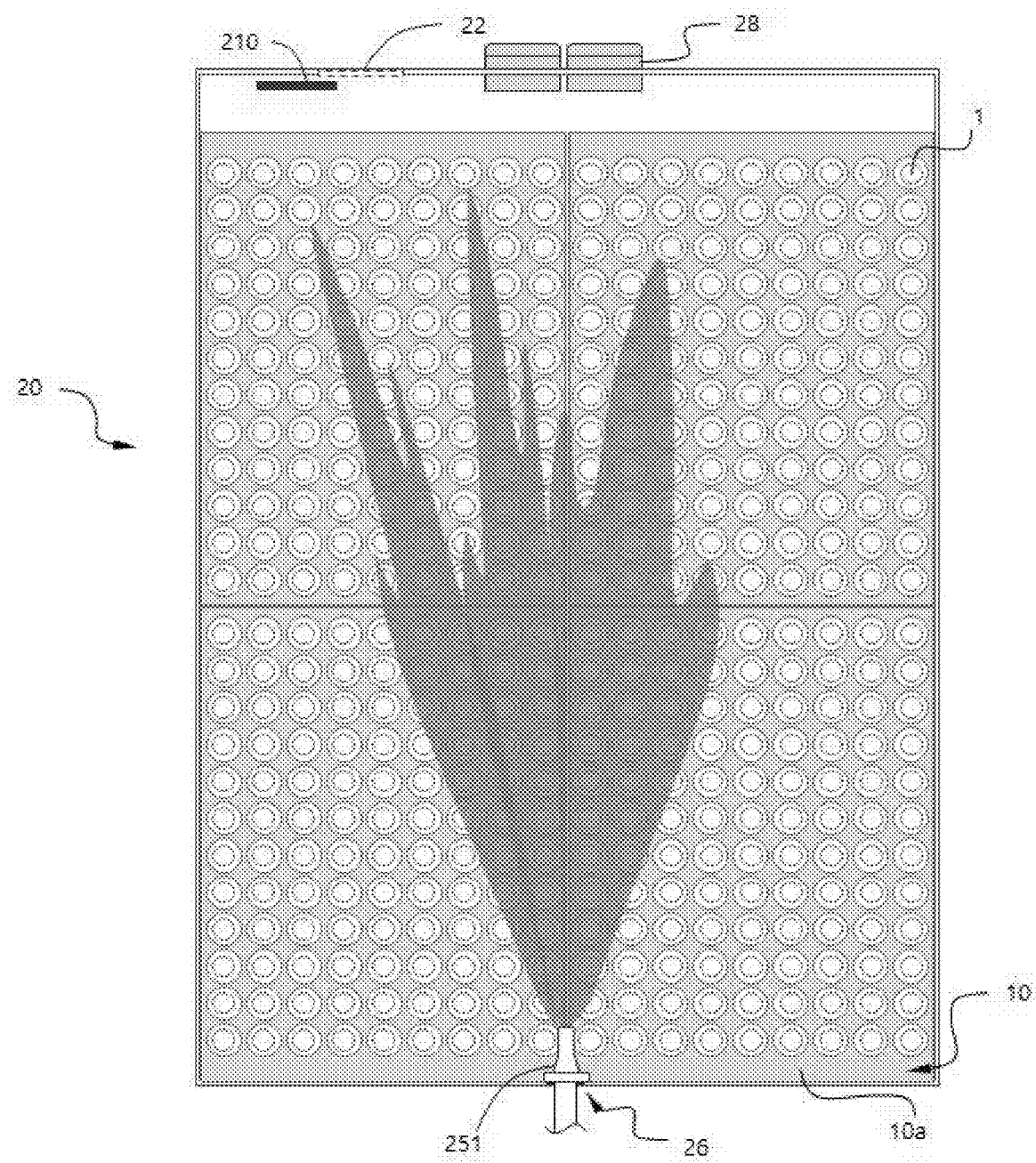
FIG. 3 is a plan view of the inside of the battery module that shows spraying a fire extinguishing agent to the top of the battery module according to an embodiment of the present disclosure.

As shown in FIG. 3, the battery module 20 may have a fire extinguishing agent spray opening 26 on a side of the module so that when fire is sensed, a fire extinguishing agent can be directly supplied into the module through the hole.

In more detail, the fire extinguishing agent spray opening 26 for supplying the fire extinguishing agent 200 into the module may be positioned to correspond to the upper space 23a or/and the lower space 23b in the module so that the fire extinguishing agent 200 smoothly moves into the module.

However, the battery module 20 according to the present disclosure is not limited only to cylindrical battery cells described above and may be applied to various types of secondary battery (a polyhedral type, a pouch type) through various changes and modifications by those skilled in the art.

Figure 4:
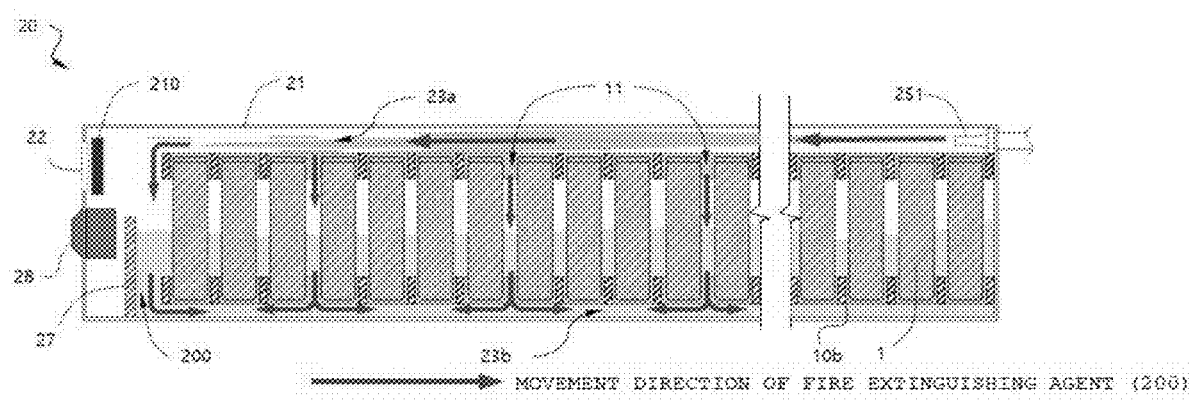
FIG. 4 is a cross-sectional view of a side of the battery module that shows movement of a fire extinguishing agent in the battery module according to an embodiment of the present disclosure.

As shown in FIG. 4, according to an embodiment of the present disclosure, the fire extinguishing agent spray opening 26 may be positioned at the upper end of the rear surface of the battery module 20 that corresponds to the upper space 23a in the module so that the fire extinguishing agent moves toward the front of the module. In FIG. 4, the front surface of the battery module is the surface on which the terminal is positioned and the rear surface is the surface positioned at the opposite side when seen from the front surface.

When a fire extinguishing agent containing water is used as the fire extinguishing agent 200, the fire extinguishing agent 200 supplied into the battery module 200 can easily leak to the outside through several gaps (e.g., a gas discharge port, an output terminal mount, a module fan mounting portion, a module case joint surface and edges, etc.). Accordingly, a plate-shaped water block fence 27 may be provided in the module, whereby it is possible to increase the cooling effect of the entire module and effectively prevent diffusion of fire due to thermal runaway and re-ignition by keeping the fire extinguishing agent up to the height of the water block fence in the module for a predetermined time.

Figure 5:
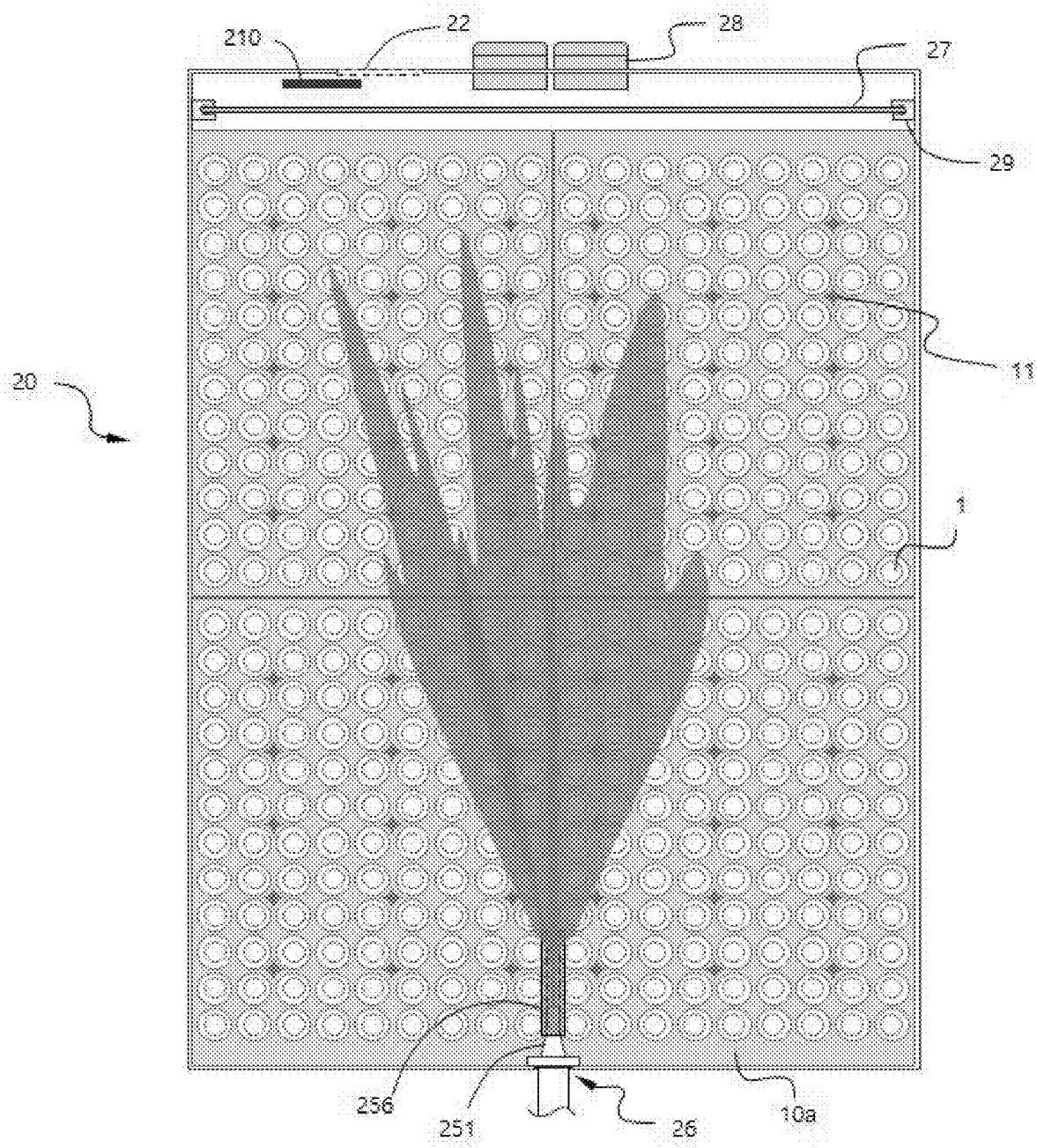
FIG. 5 is a plan view of the inside of the battery module that shows spraying a fire extinguishing agent from a spray nozzle inserted in a tube in accordance with an embodiment of the present disclosure.
Figure 6:
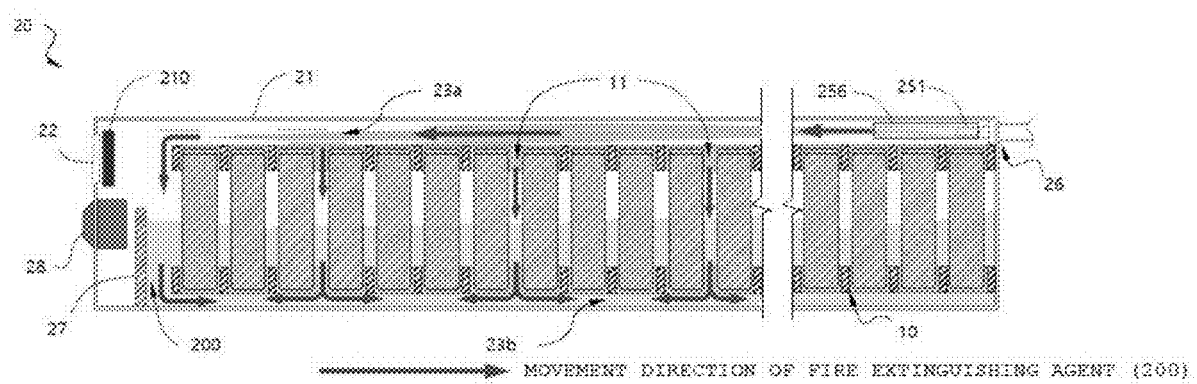
FIG. 6 is a cross-sectional view of a side of the battery module that shows movement of a fire extinguishing agent that is sprayed through the spray nozzle inserted in the tube in accordance with an embodiment of the present disclosure.

As for water block fence 27 according to an embodiment of the present disclosure, as shown in FIGS. 5 and 6, the height of the water block fence may be determined such that a predetermined portion of the battery cells 1 received in the battery module 20 is submerged in a fire extinguishing agent and the water block fence may be disposed across the space between a side of the module positioned at the end in the spray direction of a fire extinguishing agent from the spray nozzle 251 and the cell assembly member 10 positioned closest to the side.

Further, the edges of the water block fence and the floor and both sides inside the module that are in contact with the edges are finished with an adhesive waterproof finishing material, a waterproof sealing material, or a waterproof tape to prevent a fire extinguishing agent from easily leaking between them, or, as shown in FIG. 5, the edges of the water block fence may be finished with packing members 29.

Further, referring to FIGS. 5 and 6, in order to quickly and uniformly cool the bodies of the battery cells 1 densely disposed in the module, up-down through holes 11 are formed in the cell assembly member 10, so the fire extinguishing agent can uniformly move on the entire floor of the module 20.

The battery module may be provided with a spray nozzle 251 that sprays the fire extinguishing agent 200 into the module at a predetermined pressure. The spray nozzle may be inserted and fixed in the module through the fire extinguishing agent spray opening 26.

In this configuration, the spray nozzle may be a normal open type so that the fire extinguishing agent 200 can be immediately sprayed into the battery module 200 when fire is sensed. In general, fire extinguishing agent spray nozzles are equipped with a valve having a glass bulb that breaks by responding to a predetermined temperature, so such nozzles are closed normally, but when the nozzles are exposed to a predetermined temperature for a predetermined time, the glass bulb breaks, thereby opening the nozzles. However, when fire rapidly spreads in a module, the timing of suppressing the fire at an early stage may be missed due to the time that is taken to open a nozzle. Accordingly, when the spray nozzle 251 is provided in a normal open type, it is possible to supply a fire extinguishing agent into the module 20 immediately when sensing fire without consuming the time to open a nozzle.

In general, fire extinguishing agent spray nozzles are made of metal materials to resist the pressure of fluid that is sprayed, and as in the configuration of the present disclosure, when the spray nozzle 251 is directly inserted in the module 20, it may be difficult to secure an insulation distance from the cell assembly member 10. According to another embodiment of the present disclosure, the distal end portion of the open-type spray nozzle 251 is inserted in an insulating tube 256, whereby it is possible to maintain insulation by preventing direct contact between the spray nozzle and the cell assembly member. As shown in FIG. 5, for example, a first end portion of the tube 256 may receive the distal end portion of the spray nozzle 251 and a second end portion of the tube may be open and disposed in the upper space 23*a* in the module. In this configuration, the final spray point of a fire extinguishing agent is formed at the open end of the tube 256.

Figure 7A:
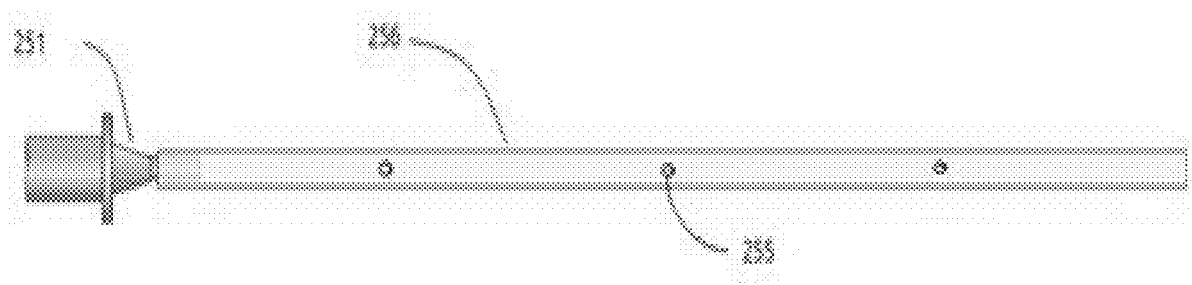
FIG. 7A is a view showing a tube having a plurality of open holes connected to a spray nozzle in accordance with an embodiment of the present disclosure.
Figure 7B:
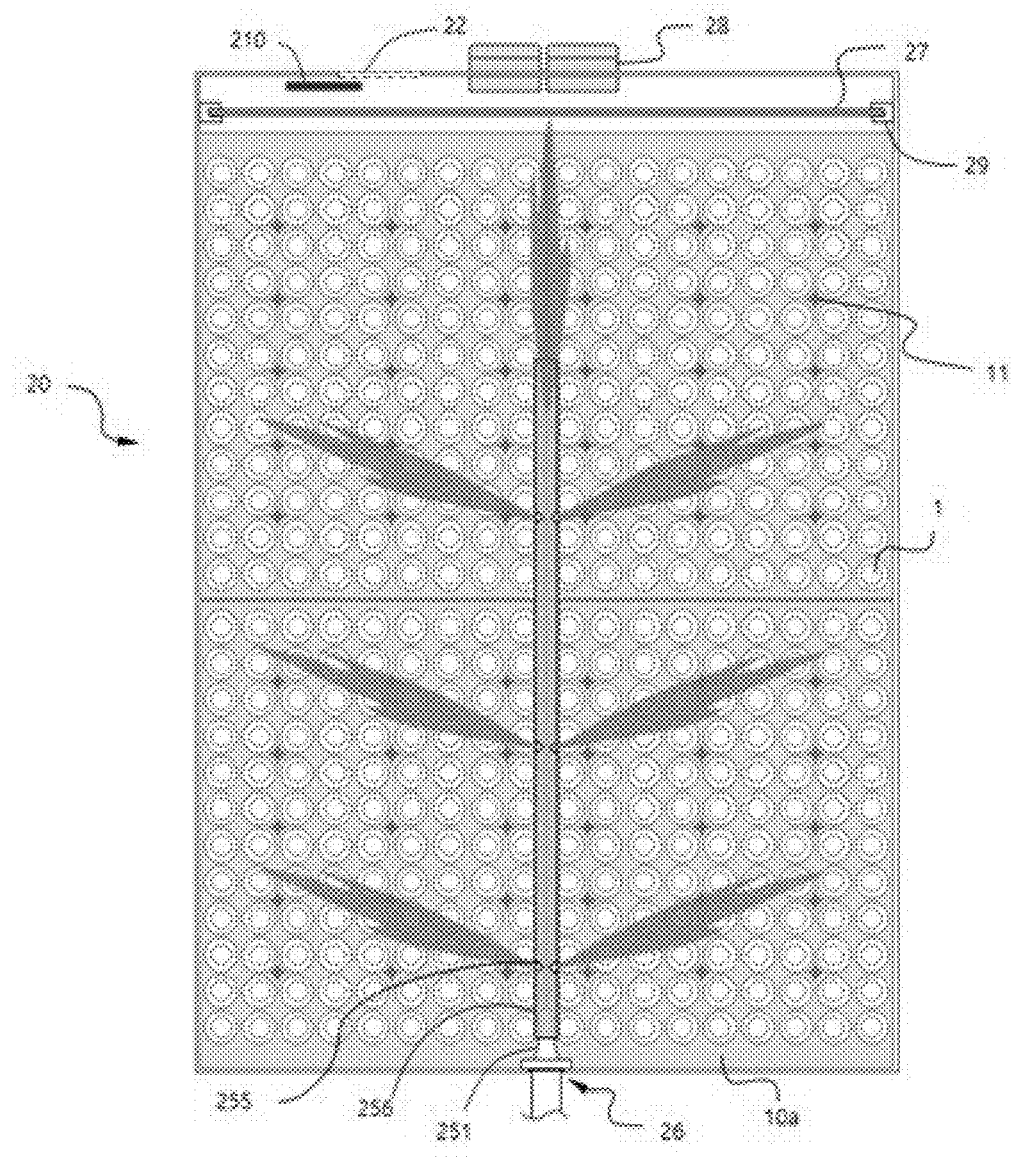
FIG. 7B is a plan view of the inside of the battery module that shows movement of a fire extinguishing agent through the tube connected to the spray nozzle in accordance with an embodiment of the present disclosure.

Further, the distal end of the tube can be positioned deep inside the upper space 23*a* by adjusting the length of the tube. In this case, as shown in FIGS. 7A and 7B in accordance with an embodiment of the present disclosure, a plurality of open holes 255 may be formed on the side of the tube in the longitudinal direction of the tube so that a fire extinguishing agent is uniformly sprayed into the module even through the side open holes 255 while the fire extinguishing agent moves in the tube.

According to another embodiment of the present disclosure, the tube may be more directly exposed to flames and high-temperature gas due to thermal runaway generated in the module. The opening at the distal end of the tube may be filled with a heat-sensitive material 257 having a predetermined length so that when the end of the tube 256 is in a closed state and the ambient temperature in the module reaches a predetermined temperature due to thermal runaway, the heat-sensitive material melts and the distal end portion of the tube opens. For example, wax of which the melting point is between 60° C. and 90° ° C. may be used as the heat-sensitive material to open the tube.

Figure 8:
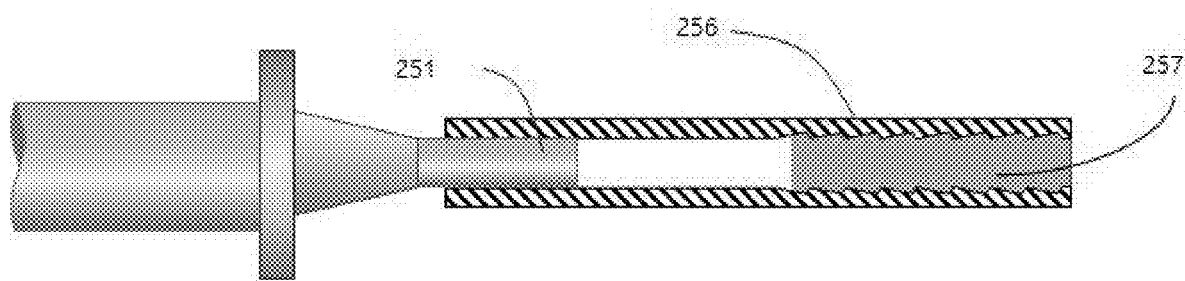
FIG. 8 is a cross-section showing a heat-sensitive material accommodated in a tube and saw tooth-shaped anti-pushing grooves formed on the inner wall of the tube in the section in which the heat-sensitive material is accommodated in accordance with another embodiment of the present disclosure.

However, when fire is sensed and the internal pressure of the tube 256 is increased by spray pressure acting in the spray nozzle, the entire heat-sensitive material 257 may be pushed out of the tube by the pressure like a cylinder. Accordingly, not only the tube 256 inserted in the problematic module 20 on fire, but also the tubes 256 inserted in surrounding normal modules 20 are opened, so it may be difficult to selectively spray a fire extinguishing agent as it intended. Accordingly, an adhesive may be added to the heat-sensitive material 257 according to an embodiment of the present disclosure to maintain the adhesive force between the inner wall of the tube and the wax even while the internal pressure of the tube 256 is increased, or, as shown in FIG. 8, saw tooth-shaped anti-pushing grooves are formed around the inner wall of the tube that corresponds to the section receiving the heat-sensitive material 257, whereby it is possible to physically prevent the heat-sensitive material from being pushed to the outside.

Figure 9:
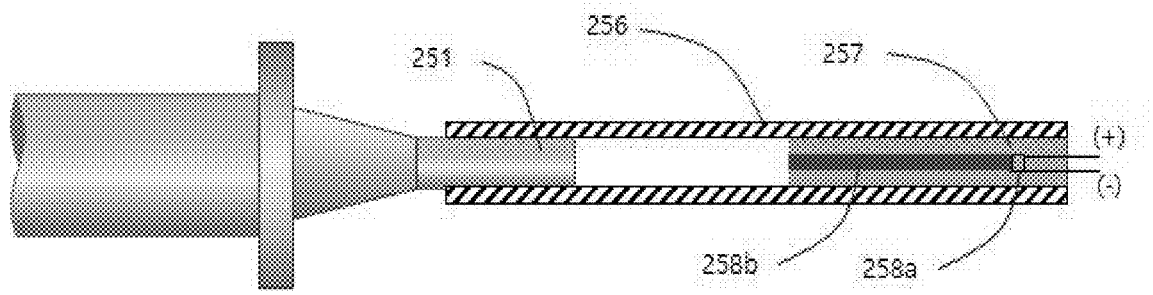
FIG. 9 is a cross-section showing a heat-sensitive material and a heat source supply member molded with the heat-sensitive material in accordance with another embodiment of the present disclosure.

For quick and immediate opening more than the passive opening type described above, a heat source supply member 258 may be molded in the heat-sensitive material 257 so that when fire is sensed, the tube is opened by instantaneously burning the heat source supply member and melting the heat-sensitive material 257 by an electrical signal. According to an embodiment of the present disclosure, as shown in FIG. 9, the heat source supply member may be composed of an ignition member 258*a* and a heat source member 258*b*, in which the ignition member is a device that locally generates high-temperature heat in an ignition terminal composed of a (+) terminal and a (−) terminal by an electrical signal so that the heat source member 258*b* starts burning. Further, the heat source member serves to increase ambient temperature within a short time through burning. In general, $Fe/KClO_4$, $Zr/BaCrO_4$, or the like is used in a solid type as the material of the heat source member and the heat source supply member may be molded with the heat-sensitive material.

When fire is sensed and an electrical signal is transmitted from the module unit fire detector 210 to the ignition member 258*a*, the ignition member can instantaneously increase the temperature of a local area. The heat source member starts burning due to the ignition member and supplies heat to the surrounding. In this process, the heat-sensitive material 257 covering the heat source supply member melts, whereby the tube can be opened. In general, since the combustion speed of heat sources is 10~50 cm/s, the tube can be opened within a short time by melting of the heat-sensitive material 257.

Since the heat-sensitive material in the tube is melted in the opening type described above, there is the advantage that it is possible to selectively spray a fire extinguishing agent only into a corresponding module 20 at an early stage.

Figure 10:
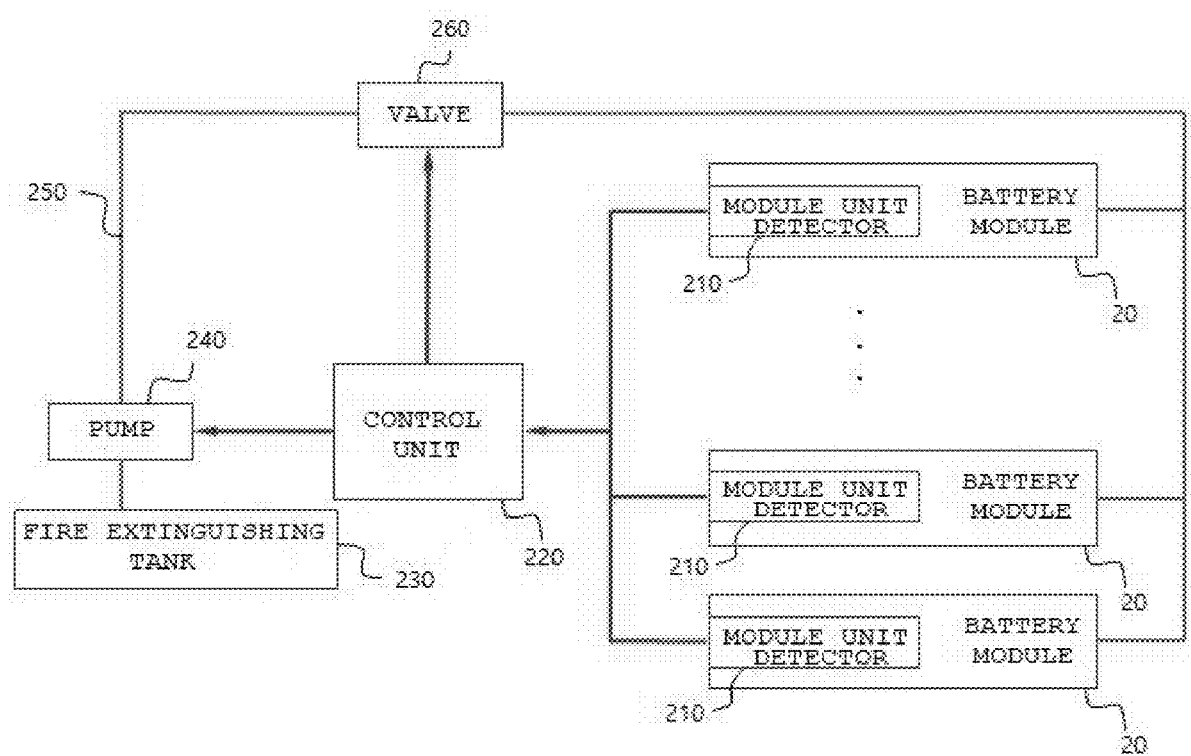
FIG. 10 is a schematic block configuration diagram of a secondary battery system including fire extinguishing equipment in accordance with the configuration of the present disclosure.

Referring to FIG. 10, the secondary battery system of the present disclosure may include at least two or more battery modules and fire extinguishing equipment.

In detail, the fire extinguishing equipment includes a fire extinguishing control unit 220, a fire extinguishing tank 230, a fire extinguishing pump 240, a pipeline 250 connected from the fire extinguishing tank to the battery modules, an on/off valve 260 disposed on any one portion of the pipeline, etc., and is at least partially coupled to the battery modules 20.

The fire extinguishing equipment of the present disclosure may be configured, as shown in FIGS. 3 to 7, to be able to suppress fire in the modules by directly spraying the fire extinguishing agent 200 into the modules when fire is sensed. In this configuration, when the fire extinguishing agent 200 contains water, the fire extinguishing agent 200 may be mixed and used with an additive to increase the cooling ability of the water. Further, a permeator that decreases the surface tension of water may be added to the additive so that the fire extinguishing agent easily permeates into the internal space of the modules 20.

As shown in FIG. 10, the fire extinguishing tank 230 receiving the fire extinguishing agent discharges the fire extinguishing agent and supplies the fire extinguishing agent to the battery modules 20 through the pipeline 250 using the fire extinguishing pump 240. The pipeline may connect the fire extinguishing tank and the fire extinguishing pump and diverge in parallel at any one position after passing through the on/off valve 260 from the fire extinguishing tank to be connected to the insides of the battery modules 20. Since the pipeline is opened at the position of the on/off valve, the fire extinguishing agent can be supplied to the modules connected to the open pipeline.

The fire extinguishing control unit 220 includes a receiver 221 that receives a fire sensing signal from the module unit fire detector 210 and a pump control member 22 that actuates the fire extinguishing pump.

Figure 11:
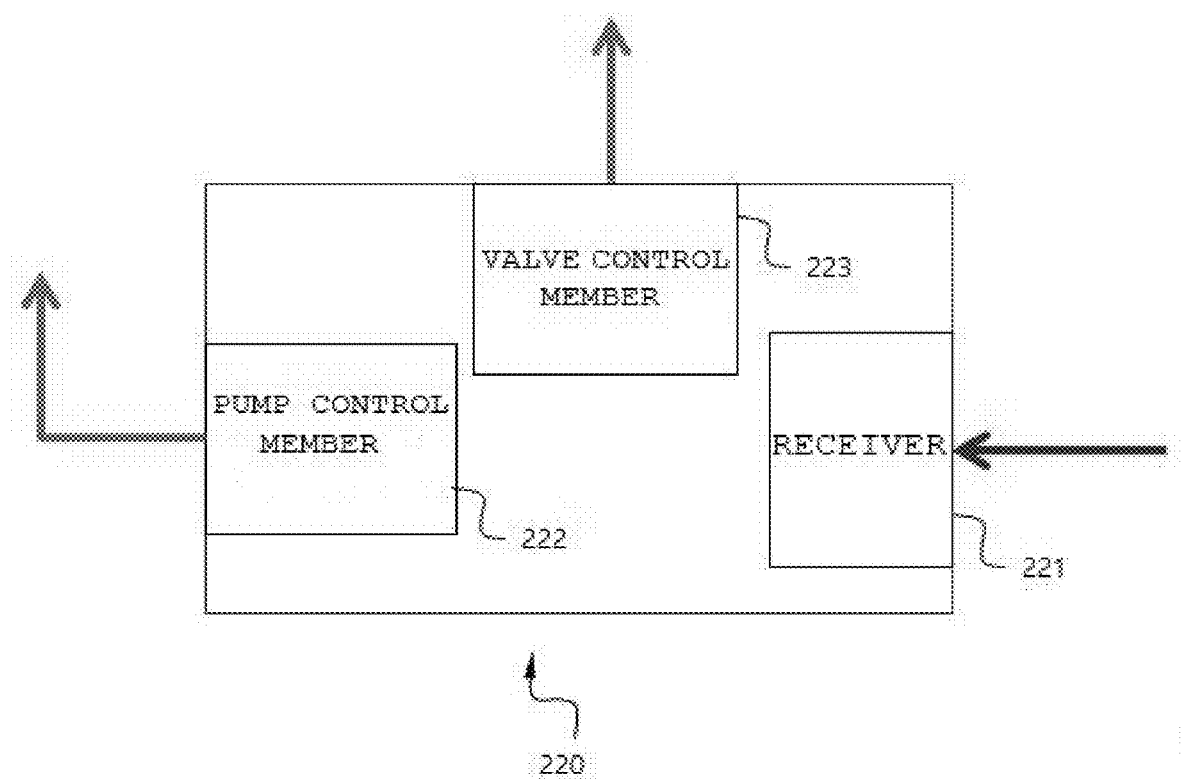
FIG. 11 is a schematic configuration diagram of a fire extinguishing control unit according to an embodiment of the present disclosure.

Referring to FIG. 10 again, the on/off valve 260 may be an active on/off valve that is normally in a closed state and can open when fire is sensed. For example, the active on/off valve may be a solenoid valve, an electric ball valve, etc. For a configuration of the present disclosure, FIG. 11 shows a schematic configuration including a valve control member 223 such that the fire extinguishing control unit 220 can control the active on/off valve 260.

Figure 12:
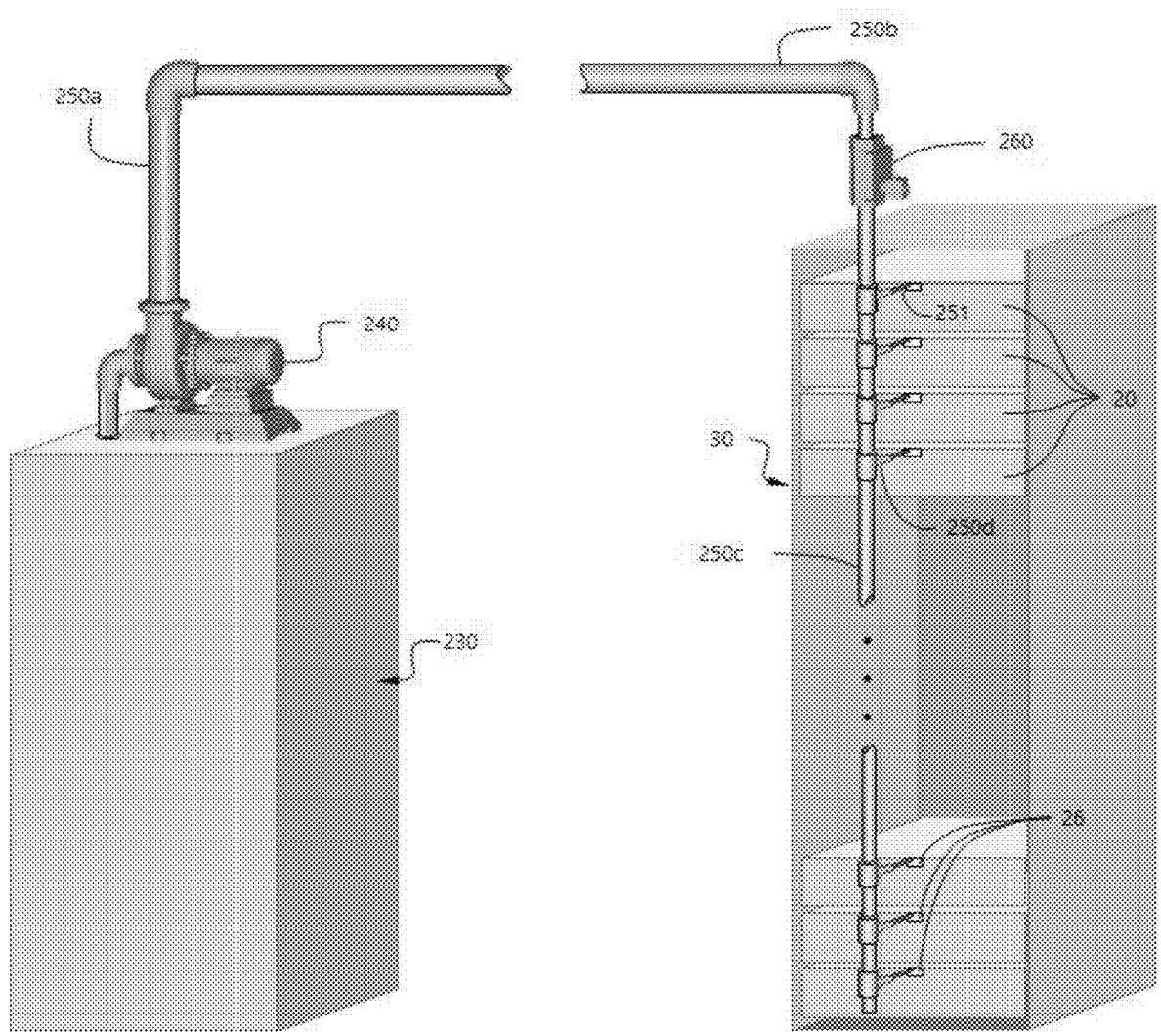
FIG. 12 is a perspective view showing a secondary battery system including fire extinguishing equipment according to an embodiment of the present disclosure.

Referring to FIG. 12 according to an embodiment of the present disclosure, a battery rack 30 may include a cabinet-type container that receives the battery modules 20 in a vertically stacked type. In order to supply the fire extinguishing agent 200 to the modules 20 received in the battery rack 30, the pipeline 250 may be composed of a common pipeline 250a extending from the fire extinguishing pump 240 into the upper portion receiving the battery rack 30, a horizontal main pipeline 250b extending horizontally at a predetermined height from the upper end of the battery rack 30 in the space, a vertical cross pipeline 250c diverging downward along a side of the battery rack 30 from the horizontal main pipeline, and branch pipelines 250d diverging in parallel horizontally from the vertical cross pipeline at positions respectively corresponding to the modules 20 received in the battery rack, and connected to spray nozzles 251 of the modules, respectively.

As shown in FIG. 12, the active on/off valve 260 is disposed at any one position on the vertical cross pipeline 250c diverging from the horizontal main pipeline 250b and opens the vertical cross pipeline when fire is sensed, so the fire extinguishing agent 200 can be supplied to all of the pipelines 250d diverging in parallel from the vertical cross pipeline.

Figure 13:
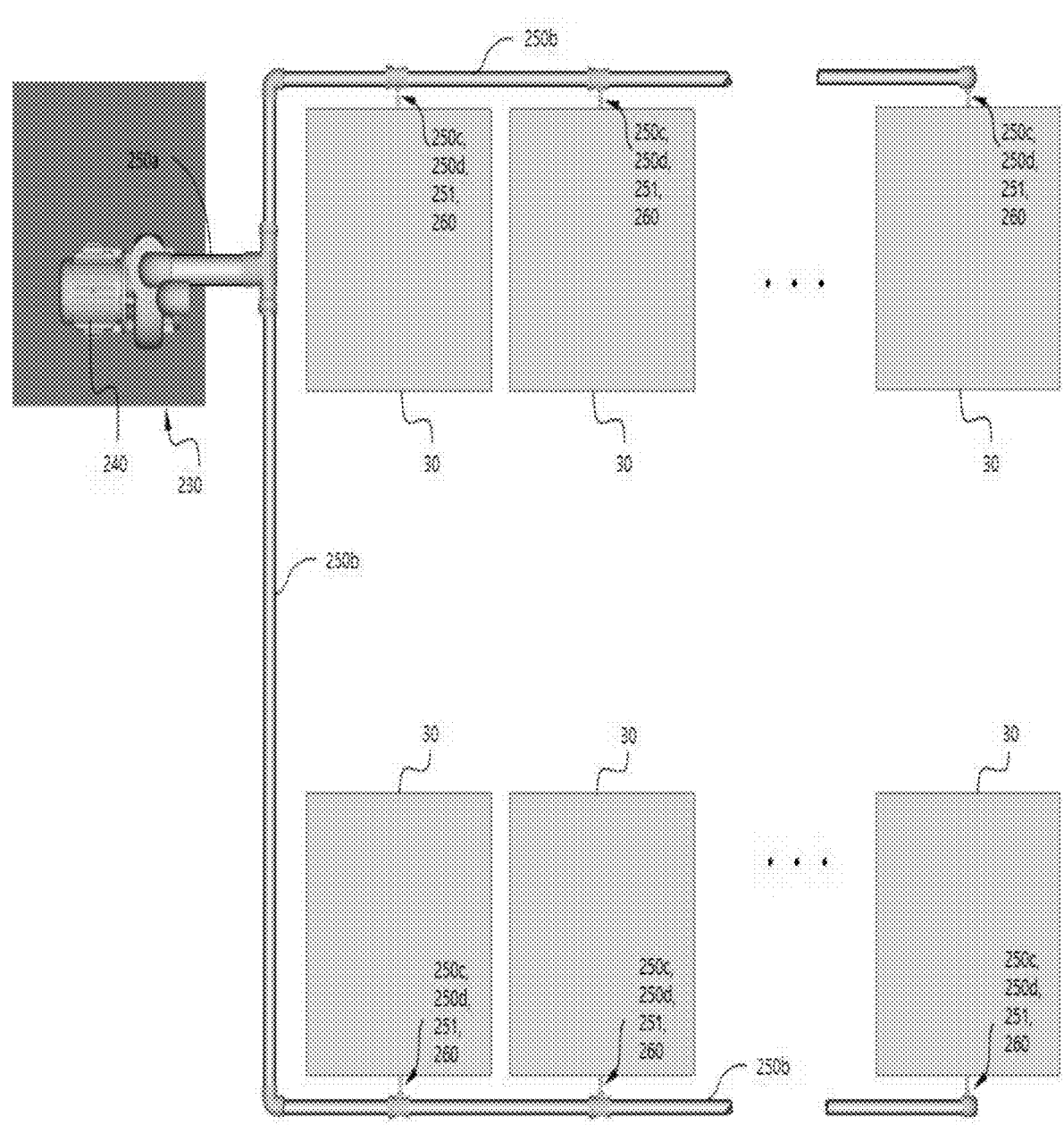
FIG. 13 is a plan view schematically showing a secondary battery system including battery racks arranged in two rows according to an embodiment of the present disclosure.

Further, the secondary battery system according to a configuration of the present disclosure may include a plurality of battery racks 30. The battery racks may be arranged in one row or two or more rows in one direction. For example, FIG. 13 is an example in which the secondary battery system includes a plurality of battery racks 30 arranged in two rows in one direction. In this configuration, the horizontal main pipeline 250b may be configured to diverge to the rows from the common pipeline 250a at the position where all of the rows of battery racks start.

Figure 14:
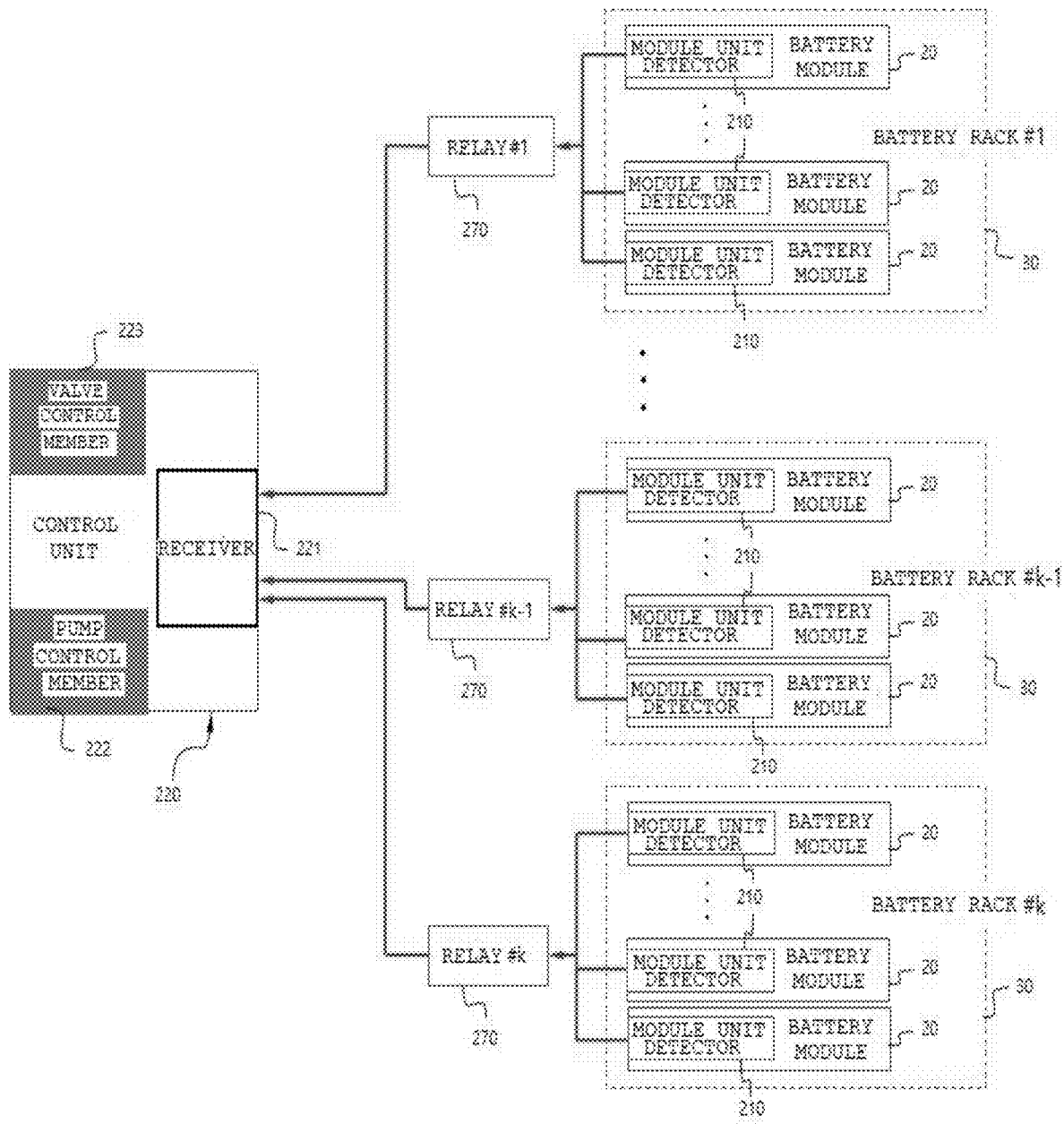
FIG. 14 is a schematic block configuration diagram showing signal relays provided respectively for battery racks and a control unit that receives signals from the signal relays in a secondary battery system including a plurality of battery racks according to an embodiment of the present disclosure.

Further, as shown in FIG. 14, the battery racks 30 each may be provided with a signal relay 270 that receives a fire sensing signal from module unit fire detectors 210 received in each battery rack 30 and transmits the fire sensing signal to the fire extinguishing control unit 220. Due to the signal relays that transmit a sensing signal, it is possible to easily determine the location of a battery rack having a problematic module and open only the valve 260 disposed on the vertical cross pipeline 250c connected with the problematic battery rack.

The invention claimed is:

1. A secondary battery system comprising:
   a cell assembly member comprising a plurality of cylindrical secondary battery cell;
   a battery module accommodating at least one or more of the said cell assembly member;
   an upper space and a lower space formed inside the said battery module and formed between the case of the said battery module and the said cell assembly member to allow a fire extinguishing agent to move into the battery module smoothly;
   a fire extinguishing agent spray opening formed on a side of the battery module to allow the fire extinguishing agent to be sprayed into the upper space or the lower space;
   a spray nozzle disposed in the said fire extinguishing agent spray opening;
   wherein the said cylindrical secondary battery cell has cylindrical shape having smaller capacity than pouch type or polyhedral type secondary battery cells, and the said spray nozzle is a permanently open nozzle for early fire extinguishing because fire spreads more rapidly inside the said battery module compared to a battery module with pouch type or polyhedral type secondary battery cells; and
   wherein the said spray nozzle is configured such that its distal end portion is inserted in one end of a tube made of a certain length of insulation material, and the other end of the said tube having a circular cross-section is disposed in the said upper space;
   and further comprising an ignition member for the ignition of a heat source member by an electrical signal, and a heat source supply member comprising a heat source member connected to and ignited by the said ignition member; and
   wherein the said heat source supply member is molded with a heat-sensitive material, and
   wherein the other end of the said tube is filled with the heat-sensitive material so that the opening of the other end of the said tube is closed by the heat-sensitive material, and
   wherein the heat source member burns through the ignition of the said ignition member when a fire is detected and the heat-sensitive material increases in temperature and melts, whereby the said tube opens.

2. The secondary battery system of claim 1, wherein a plurality of the said battery module is arranged in a predetermined direction and electrically connected; and
   the said secondary battery system further comprises a fire extinguishing equipment comprising a fire extinguishing agent which is water or a fire extinguishing substance mixed with water; a fire extinguishing tank configured to receive the said fire extinguishing agent; a pipeline connected from the fire extinguishing tank to the spray nozzle disposed in the extinguishing agent spray opening of each of battery modules; a valve disposed on the said pipeline for the purpose of controlling the supply of the said fire extinguishing agent to each of the said battery modules; a control unit comprising a fire extinguishing pump configured to move the fire extinguishing agent through the pipeline from the fire extinguishing tank, a receiver for receiving a fire detection signal, and a pump control member to actuate the said fire extinguishing pump.

3. The secondary battery system of claim 2, wherein the said valve is an active on/off valve; and the said control unit further comprises a valve controller configured to open the said active on/off valve when fire is detected.

* * * * *